United States Patent [19]

Zambelli

[11] Patent Number: 4,619,272

[45] Date of Patent: Oct. 28, 1986

[54] INSTRUMENT FOR CARRYING OUT BIOPSIES ON TISSUES REMOVED FROM ORGANS TO BE EXAMINED

[76] Inventor: Roberto Zambelli, Via Borsa, 69, Milan, Italy

[21] Appl. No.: 754,844

[22] Filed: Jul. 12, 1985

[30] Foreign Application Priority Data

Jul. 31, 1984 [IT] Italy ............................ 22756/84[U]

[51] Int. Cl.⁴ ............................................. A61B 10/00
[52] U.S. Cl. .................................. 128/753; 128/310; 604/117; 604/231
[58] Field of Search ............... 128/310, 752, 753, 312; 604/117, 231

[56] References Cited

U.S. PATENT DOCUMENTS

| 2,864,364 | 7/1954 | Mizzy ................................. 604/231 |
| 3,487,834 | 8/1967 | Smith, Jr. et al. .................. 604/117 |
| 4,142,517 | 3/1979 | Stavropoulos et al. ............ 128/310 |
| 4,203,444 | 5/1980 | Bonnell et al. ...................... 128/752 |

OTHER PUBLICATIONS

"Multiple-Retrieving Small-Intestinal Biopsy Tube", S. J. Baker et al., *The Lancet*, Sep. 24, 1960, p. 686.

*Primary Examiner*—William E. Kamm
*Assistant Examiner*—Randy Citrin
*Attorney, Agent, or Firm*—Darby & Darby

[57] ABSTRACT

The instrument comprises an outer cylindrical body 3 leading off at one end 3a to a biopsy cannula 5, and a piston 4 slidably engaged within said outer cylindrical body 3 with which it defines a suction chamber 10. The piston carries, at one end, a stylet 6 engaging with play inside said biopsy cannula 5 and is provided with a grip member 15 which slidably engages into a pair of longitudinal guides 13, 14 obtained in the outer cylindrical body 3, a stroke-limiting member 31 being disposed in an adjustable position on said outer cylindrical body 3.

8 Claims, 4 Drawing Figures

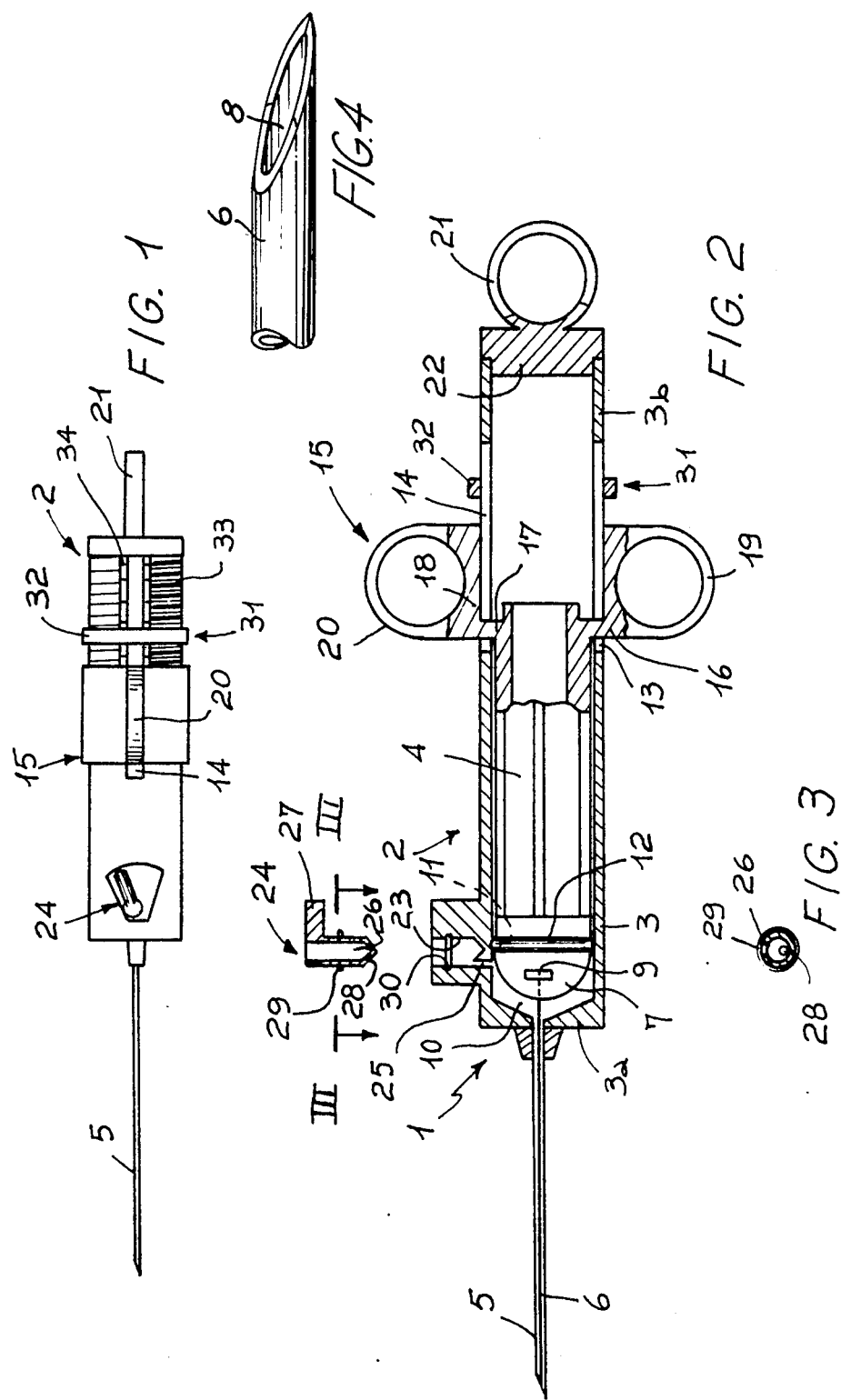

INSTRUMENT FOR CARRYING OUT BIOPSIES ON TISSUES REMOVED FROM ORGANS TO BE EXAMINED

FIELD OF THE INVENTION

The present invention relates to an instrument for carrying out biopsies or tissues removed from organs to be examined, of the kind comprising a syringe essentially consisting of an outer cylindrical body leading off, at one end, to a biopsy cannula, and of a piston slidably engaged within said outer cylindrical body with which it defines a suction chamber and carrying, at one end, a stylet engaging with play inside said biopsy cannula.

BACKGROUND OF THE INVENTION

It is known that biopsy is an operation allowing a surgeon to remove a certain amount of tissue from a living body for the purpose of examining it in a laboratory.

In order to carry out this operation it is necessary to have instruments adapted to penetrate the organ to be examined while causing the minimum traumatism to patients by virtue of a very rapid action. Furthermore, these instruments must be capable of removing a rather important amount of tissue so that all necessary analyses can be performed thereon.

For the purpose needle-like instruments usually called biopsy needles are commonly used. Among them a very efficient needle is the so-called Menghini needle, by the name of its inventor. This instrument substantially consists of a syringe the outer cylindrical body of which is connected at one end to a biopsy cannula or hollow needle. Inside said outer cylindrical body is slidably engaged a piston carrying at one end a needle-like stylet adapted to slidably engage in the cannula of the outer cylindrical body. Said stylet consists of a metal thread-like element provided with a longitudinal milling adapted to allow the suction to be transmitted inside the biopsy chamber when the piston, which defines a suction chamber together with the outer cylindrical body, is suitably drawn in the cylindrical body itself.

In this kind of needle, while the outer biopsy cannula is suitably sharpened for cutting, the stylet has a penetrating conical point normally projecting from the cannula.

The above described instrument is used, as already said, for dissecting and drawing a certain amount of tissue from organs to be examined. Said organs may be for example the liver, the prostate or even an unknown mass such as that of a tumor, in order to determine the type of neoplasm concerned and consequently the exact therapy to be performed.

Supposing that it is necessary to reach the liver in order to remove a certain amount of tissue, the instrument is used in the following manner. The syringe is first maintained with the piston inserted at the bottom of the outer cylindrical body. In this condition, with the stylet point projecting from the cannula, the needle is caused to penetrate under the dermis; it crosses the subcutaneous fats and comes close to the liver without removing any tissue. At this point the surgeon puts the syringe under suction so that the stylet disappears inside the cannula up to a stop member disposed on the syringe for the purpose of avoiding the cylindrical body-piston assembly being maintained pulled by the surgeon itself.

Now, by a quick motion, the biopsy cannula is caused to penetrate into the liver; so it dissects the tissue and is filled with the same, assisted by the vacuum previously produced in the suction chamber. Then it is necessary to withdraw the cannula from the body together with the dissected tissue which is called biopsy fragment.

Always by effect of the vacuum created inside the syringe, the fragment is retained inside the cannula being withdrawn, until it is torn at its bottom and remains therefore in the cannula itself which is still under vacuum. Afterwards the piston must be pushed inside the syringe again in order to eliminate the vacuum and to cause the stylet to eject the removed fragment.

However the above described instrument, notwithstanding its undoubted technical and operative advantages, has some drawbacks.

A first drawback resides in that, when it has to deal with rather compact tissues such as those of a liver suffering from cirrhosis or with a very fibrous tumor or a rather hard prostate, it does not succeed in tearing the fragment off owing to the insufficient vacuum determined inside the syringe. Therefore the use of this instrument appears rather limited above all where the oncologic field is concerned.

In fact it has been noticed that when the needle comes close to the organ to be submitted to biopsy and the syringe is disposed under vacuum before penetrating the organ to be examined, blood and other physiological liquids are drawn inside the syringe and when afterwards the organ is penetrated by the cannula, the latter further fills up with blood and tissue so that the vacuum inside the syringe drops. In other words, the maximum vacuum state occurs at the beginning of the biopsy cannula penetration into the organ to be examined, while the maximum vacuum should be desirable at the moment of the cannula extraction from the organ due to the fact that a high vacuum state facilitates the fragment tearing off.

A further drawback of this type of instrument resides in that the penetration into the organ, for example the liver, requires as rapid a movement as possible because said penetration takes place between two ribs and therefore the patient might react by a sudden movement which would cause the needle to move inside the liver giving rise to well imaginable damages.

Furthermore, under that circumstance, a further drawback is given by the fact that the surgeon does not succeed in controlling the penetration with the risk of passing the organ being examined right through. The latter drawback is mainly due to the fact that it is practically impossible to adjust the needle penetration.

It should also be understood that should an unknown mass be examined, which could be a tumor as big as a walnut, the through penetration of that mass would be rather easy which could cause the insemination of parts of that tumor to not yet infected organs.

Beside these primary disadvantages, it is also possible to detect further disadvantages of less consequence such as for example the fact that the syringe must be operated with both hands, whilst it should be desirable to carry out the operation using only one hand.

Finally, a further drawback is represented by the shape of the stylet which, having a conical point, causes, at its penetration into the organ, tearings that heal up with more difficulty with respect to the clear cuts produced by the cutting point of a stylet consisting of a cannula provided with a three-side sharpening.

OBJECTS

It is therefore a general object of the present invention to provide an instrument for carrying out biopsies on tissue removed from organs to be examined which is capable of obviating the above mentioned drawbacks.

Within the scope of this general object, the primary object of the present invention is to make available a new instrument which is adapted to reach the fragment and tear it off while maintaining the maximum vacuum inside the syringe, which results in a remarkable increase in the possibilities of a successful operation.

A further fundamental object of the present invention is the possibility of pre-setting the penetration into the organ to be examined in order to prevent the needle from penetrating too little or too much coming therefore out of the opposite side.

A further object of the present invention is to make available an instrument that during the operation step can be operated quickly and with one hand only.

A still further object of the invention is the possibility of ejecting all cells that may eventually adhere to the inner surface of the biopsy cannula in order to allow a cytological reading.

SUMMARY OF THE INVENTION

The above and still further objects that will become more apparent in the following are attained, according to the present invention, by an instrument for carrying out biopsies on tissues removed from organs to be examined, comprising a pair of opposite longitudinal guides obtained in the outer cylindrical body, a grip member for the piston, which slidably engages within said guides, a stroke-limiting member disposed in an adjustable position on the outer cylindrical body and designed for abutting against said piston's grip member, the stylet consisting of a hollow needle defining an air path leading off to the inside of the suction chamber through at least one slit provided inside the piston.

BRIEF DESCRIPTION OF THE DRAWINGS

Further features and advantages of the invention will become more apparent from the detailed description of an instrument for carrying out biopsies on tissues removed from organs to be examined given hereinafter by way of example only with reference to the accompanying drawings, in which:

FIG. 1 is a front view of the instrument according to the invention;

FIG. 2 is a sectional side view to an enlarged scale of the instrument seen in FIG. 1, with the air intake valve in a broken away condition;

FIG. 3 shows a section taken along the line III—III of the valve body seen in FIG. 2; and FIG. 4 is an enlarged perspective view of a portion of the instrument according to the invention.

DESCRIPTION OF THE PREFERRED EMBODIMENT

Referring to the drawings and particularly to FIGS. 1 and 2, it has been generally indicated at 1 an instrument for carrying out biopsies on tissues removed from living bodies to be examined.

This instrument substantially comprises a syringe 2 consisting of an outer cylindrical body 3 within which a piston 4 is slidably engaged. On the outer cylindrical body 3 and exactly at one end 3a thereof, a biopsy cannula 5 is mounted within which a stylet 6 carried by the head 7 of piston 4 slidably engages.

According to a feature of this invention, the stylet 6 comprises a hollow needle having a three sided, sharpened point (as shown in FIG. 4), that is, a tip that is cut diagonally according to three different angles on different planes. The hollow needle defines an air path 8 leading off, through at least a slit 9 obtained in the head 7 of piston 4, into a suction chamber 10 defined by the bottom wall of the outer cylindrical body end 3a and the head 7 of piston 4.

For the purpose of avoiding leaking of air along the inner side walls of the syringe, at least an annular groove 11 is provided on the head 7 which is designed for housing a corresponding seal 12 (FIG. 2).

Always referring to FIG. 2, a pair of opposite longitudinal guides 13 and 14 are provided in the outer cylindrical body 3 of syringe 2; they consist for example of slits into which a grip member for the piston 4 generally identified at 15 engages. Said grip member comprises a pair of opposite projections 16 and 17 provided in the rear part of piston 4 and connected to each other by an annular support 18 surrounding the outer cylindrical body 3 of syringe 2. The annular support 18 carries a pair of opposite grip rings 19 and 20 integral thereto and designed for the introduction of two fingers by the surgeon when a biopsy has to be performed. A third finger, the thumb, must instead be introduced into a further grip ring 21 carried by a stopper 22 closing the outer cylindrical body 3 at its end 3b opposite the end carrying the cannula 5.

Still referring to FIG. 2, 23 designates a seat for an air intake valve 24 that opens through a duct 25, in the suction chamber 10 of syringe 2. The valve 24 essentially consists of a cylindrical valve body 26 and of an actuating lever 27. A through hole 28 is provided in the cylindrical body 26 said hole being adapted to bring the environmental air into communication with the suction chamber 10 through duct 25 after the removal of the desired quantity of tissue, in order to facilitate the fragment ejection. The valve 24 is sealingly mounted in its respective seat 23 and for the purpose a seal ring 29 is provided which is designed for being accommodated within a corresponding annular groove 30 obtained on the wall of the valve seat 23.

Turning now to FIG. 1, and according to a further very important feature of the invention, the syringe 2 is provided with a stroke-limiting member generally indicated at 31. Said member is disposed in an adjustable position on the outer cylindrical body 3 of the syringe and has the task of limiting the penetration of cannula 5 into the organ to be examined in a very precise manner, when, by virtue of the penetrating action of stylet 6, the operator has come close to said organ. The stroke-limiting member 31 substantially comprises a ring 32 provided with an inner thread allowing the same to be screwed up on a corresponding thread 33 obtained on the outer surface of the outer cylindrical body 3.

Advantageously, a graduated scale 34 is also provided on said outer cylindrical body 3; it is designed for indicating the desired biopsy penetration, depending upon the different operative conditions.

Said ring 32 is intended for abutting, when the instrument is being used, against the annular support 18 of the grip member 15 for piston 4.

OPERATION

After describing the instrument of the invention mainly from a structural point of view, the operation of the same will now be illustrated.

First the ring 32 is disposed in a determined position corresponding to the progress distance of the cannula inside the organ to be submitted to biopsy and the lever 27 of valve 24 is set in its closing position; then the surgeon begins the penetration pushing with his middle finger and forefinger introduced into the rings 18 and 19. Under this situation the piston 4 is located at the bottom of the end 3a of the outer cylindrical body 3 and the point of stylet 6 projects from the cannula. While maintaining these conditions, the surgeon pushes in until he reaches the organ to be submitted to biopsy. After attaining this position, while holding the grip member 15 at a standstill, the operator presses his thumb on the stopper 22 of the outer cylindrical body 3 causing the same to progress, which results in a progress of cannula 5 with respect to the stylet 6. This progress will go on until the ring 32 abuts against the annular support 18 of the grip member 15.

Under this situation, an increasing vacuum is created inside the suction chamber 10, said vacuum reaching its highest value as soon as the ring 32 abuts against the grip member 15. By virtue of this vacuum, a certain amount of tissue can be removed from the concerned organ and extracted exactly when the maximum vacuum is attained inside the suction chamber 10. Due to the above conditions, the fragment can be easily torn off by a rapid operation requiring the use of one hand only on the part of the operator.

It should be understood that the removal and extraction take advantage of the fact that the stylet 6 consists of a hollow needle inside which, as well as inside the hollow space defined by the stylet itself and the cannula 5, a useful vacuum state is created. In addition, said stylet allows the suction of liquids and cells into its inner cavity.

Once the fragment has been extracted from the patient's body, the valve 24 is brought to its opening position so that there is the introduction of air into the suction chamber 10; during the following pushing step of piston 4 said air promotes not only the ejection of the removed fragment but even that of possible cells adhering to the inner cannula walls.

If during this step one wishes to separate the compact histological tissue from the cytological liquid, it will be sufficient first to eject the histological tissue by means of the stylet 6 and next, after opening the valve 24 aspirating air into the syringe and closing it again, to eject the cytological liquid, together with the air, on a microscope slide.

For the purpose and where necessary it is also possible to increase the volume of air aspirated into the suction chamber 10 by suitably disposing the ring 32 so that the piston stroke may be lengthened.

It should be understood that, if desired, the instrument according to the invention could be used in the traditional manner too; in fact it is also possible to enter the organ to be submitted to biopsy and to create the vacuum by a return movement of the piston inside the syringe, all that being obtained by the use of one hand only. In this case however it is not possible to take advantage of the useful effects determined by the presence of means for adjusting the instrument penetration; in fact when the operator comes close to the organ to be examined, he must push the instrument in without any possibility of limiting its stroke.

The instrument according to the invention attains the intended purposes.

Obviously, many modifications of a practical nature may be made to the constructional details of the instrument according to the invention without in any way deviating from the technical solution described above and claimed hereunder.

What is claimed is:

1. An instrument for performing biopsies on tissues removed from organs to be examined, which comprises:
    an outer cylindrical body;
    a hollow, biopsy cannula affixed to one end of the cylindrical body; the means cannula having an organ penetrating tip;
    a piston slidably movable within the cylindrical body, the piston and the cylindrical body defining a suction chamber, the piston including a slit formed therein, the suction chamber communicating with the interior of the biopsy cannula;
    a stylet slidably movable within the cannula and operatively coupled to the piston, the stylet having a hollow needle defining an air path communicating with the suction chamber; through the slit formed in the piston
    a pair of oppositely disposed longitudinal guides formed on the cylindrical body;
    grip means for effecting movement of the piston relative to the body, the grip means being slidably mounted within said guides and operatively coupled to the piston so as to be movable therewith; and
    stroke limiting means for limiting the movement of the grip means with respect to the body, the stroke limiting means being mounted and adjustably positioned on the cylindrical body and adapted to abut the grip means.

2. The instrument according to claim 1 wherein said stylet consists of a hollow needle provided with a three-side sharpened point.

3. An instrument as defined by claim 1, which further includes:
    an air intake valve adapted to be selectively opened, the air intake valve selectively communicating with the suction chamber to facilitate the ejection of citologic liquid together with tissue after tissue abstraction has been performed; and
    a valve seat formed in the cylindrical body for receiving the air intake valve.

4. An instrument as defined by claim 1, wherein the grip means includes a pair of opposite projections mounted on the piston and slidably movable within the longitudinal guide, an annular support integrally joined to the projections and surround the cylindrical body, and a pair of opposite grip rings mounted on the annular support.

5. An instrument as defined by claim 1, which further includes a grip ring mounted on the cylindrical body at the other end thereof.

6. An instrument as defined by claim 1, wherein the stroke limiting means includes an inwardly threaded ring; and wherein the cylindrical body includes a threaded outer surface formed on a portion thereof, the threaded ring engaging the threaded surface of the body.

7. An instrument as defined in claim 6, which further includes a graduated scale positioned adjacent the threaded surface of the cylindrical body, the scale being adapted to indicate the maximum volume defined by the suction chamber.

8. The instrument according to claim 3, wherein said valve comprises a cylindrical body sealingly inserted into said valve seat, a through hole being provided in said cylindrical body which hole, when the valve is in its opening condition, is brought into communication with a duct for the introduction of air into the suction chamber.

* * * * *